US009232982B2

(12) United States Patent
Soler et al.

(10) Patent No.: US 9,232,982 B2
(45) Date of Patent: Jan. 12, 2016

(54) SYSTEM FOR ORIENTATION ASSISTANCE AND DISPLAY OF AN INSTRUMENT IN AN OBJECT UNDER EXAMINATION PARTICULARLY FOR USE IN HUMAN BODY

(75) Inventors: Luc Soler, Wolfisheim (FR); Jacques Francois Bernard Marescaux, Scharrachbergheim (FR); Stephane Nicolau, Strasbourg (FR); Klaus-Martin Irion, Emmingen-Liptingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 350 days.

(21) Appl. No.: 12/797,209

(22) Filed: Jun. 9, 2010

(65) Prior Publication Data

US 2011/0069159 A1    Mar. 24, 2011

(30) Foreign Application Priority Data

Jun. 10, 2009    (DE) .......................... 10 2009 025 077

(51) Int. Cl.
*H04N 7/18*    (2006.01)
*A61B 19/00*    (2006.01)

(52) U.S. Cl.
CPC ............. *A61B 19/52* (2013.01); *A61B 19/5212* (2013.01); *A61B 2019/5251* (2013.01); *A61B 2019/5261* (2013.01); *A61B 2019/5289* (2013.01); *A61B 2019/5293* (2013.01)

(58) Field of Classification Search
CPC ............. H04N 7/18; A61B 5/00; A61B 1/04; A61B 5/05
USPC .................... 348/65; 600/109, 424, 104, 585; 700/226
See application file for complete search history.

(56) References Cited

U.S. PATENT DOCUMENTS 6,275,718 B1 *   8/2001   Lempert ...................... 600/407
6,359,647 B1 *   3/2002   Sengupta et al. ............. 348/154

(Continued)

FOREIGN PATENT DOCUMENTS

DE           20001134 U1    5/2000
DE      102005019143 A1    11/2006

(Continued)

OTHER PUBLICATIONS

European Search Report; Application No. EP 10 00 5943; Sep. 16, 2010; 3 pages.

*Primary Examiner* — Geepy Pe
*Assistant Examiner* — Salame Amr
(74) *Attorney, Agent, or Firm* — Whitmyer Group LLC

(57) ABSTRACT

A system for orientation assistance and display of an instrument that is inserted or present in the natural or artificially produced hollow cavity (human, animal, object), and that is equipped with one or more sensor units. Multiple measurements of the 3D position of the instrument equipped with one or more sensor units are performed by positioning a measuring system, so that a precise orientation and positioning of the instrument in the body can be computed. The 3D position data are used to compute a virtual image of the instrument synchronously. The virtual images are then either projected directly in exact position onto the body surface of a person or combined in a body surface image (real video camera image of the patient) onto a monitor or superimposed (virtual or augmented reality). The system is especially appropriate for displaying for a user a medical instrument, such as a catheter or a rigid or flexible endoscope, in the body of a person in real time, extracorporeally and in correct position.

15 Claims, 3 Drawing Sheets

(56) References Cited

U.S. PATENT DOCUMENTS

| | | | |
|---|---|---|---|
| 2002/0052546 A1* | 5/2002 | Frantz et al. | 600/424 |
| 2004/0133129 A1* | 7/2004 | Harari et al. | 600/585 |
| 2004/0204645 A1 | 10/2004 | Saadat et al. | |
| 2005/0033142 A1* | 2/2005 | Madden et al. | 600/407 |
| 2006/0281971 A1* | 12/2006 | Sauer et al. | 600/109 |
| 2007/0002038 A1 | 1/2007 | Suzuki et al. | |
| 2008/0047567 A1 | 2/2008 | Bonutti | |
| 2008/0086051 A1* | 4/2008 | Voegele | 600/424 |
| 2009/0198371 A1* | 8/2009 | Emanuel et al. | 700/226 |
| 2010/0317919 A1* | 12/2010 | Takaoka et al. | 600/104 |

FOREIGN PATENT DOCUMENTS

| | | |
|---|---|---|
| EP | 1738709 A1 | 1/2007 |
| EP | 1982650 A1 | 10/2008 |
| EP | 2123232 A1 | 11/2009 |
| JP | 2000350734 A | 12/2000 |
| WO | 2006116597 A2 | 11/2006 |
| WO | 2008093517 A1 | 8/2008 |

\* cited by examiner

SYSTEM FOR ORIENTATION ASSISTANCE AND DISPLAY OF AN INSTRUMENT IN AN OBJECT UNDER EXAMINATION PARTICULARLY FOR USE IN HUMAN BODY

CROSS-REFERENCE TO RELATED APPLICATIONS

The present application claims priority of German patent application No. 10 2009 025 077.8 filed on Jun. 10, 2009.

FIELD OF THE INVENTION

The present invention relates to a system for orientation assistance and display of an instrument in an object under examination, in particular an endoscope for use in the human or animal body.

BACKGROUND OF THE INVENTION

There are already various processes and devices in the art that demonstrate the combination of minimally invasive endoscopic procedure methods with augmented reality and image data supported techniques (R. Mösges, Die Methodik computergestützten Operierens. Habilitationsschrift, 1992, Hochschule Ascher).

Thus the three-dimensional display of the organ systems (individual internal patient anatomy), based first on pre-operatively acquired image data of a 3D-CT or MRT scanner, is ascertained and viewed on a monitor. The position and orientation, for instance, of an endoscope are then imaged and displayed in the three-dimensional image of the interior of the body.

Patent WO 2006/116597 A2 describes a system for navigational examination of medical instruments. Here an endoscope, equipped with a position sensor, is followed in the body of a human patient on the basis of its 3D positions. Here, first by means of a computer tomograph, images are taken as a basis for producing a virtual image of the interior of the body. The virtually ascertained image is then displayed on a monitor. Likewise, a symbol of the endoscope is also superimposed on this monitor. The disadvantage, however, is that the entire length of the instrument is not displayed and can only be poorly captured.

The disadvantage of these processes is that in order to be able to construct an augmented-reality application, it is necessary at first, preoperatively, to provide an entire system, which is expensive as well as complex to operate, consisting of video camera, tracking devices, nuclear spin tomographs, support software, and so on. In addition, the aforementioned methods have the great disadvantage that, before and sometime even during a single procedure, a number of x-ray images are required to produce the virtual image of the body interior by means of a computer tomograph (CT). This means a high radiation exposure for the patient as well as for the operating room personnel. In addition, in the event of an emergency intervention, there is often insufficient time to be able to provide the corresponding ED image data from computer tomography preoperatively. The result is that the physician in these procedures is deprived of important information for the spatial orientation.

It is therefore the object of the present invention to provide a system for orientation in an object under examination that reduces radiation exposure before and during a procedure, fulfills real-time requirements as much as possible, is simple to operate and in particular allows an inexperienced physician to have an improved and rapid orientation and display of an instrument inserted into an object under examination.

SUMMARY OF THE INVENTION

This object is achieved according to the invention through the attributes of the independent claims. The subsidiary claims elaborate on additional ideas of the invention in particularly advantageous manner.

According to the invention, therefore, a system for orientation assistance and display of medical instruments in objects under examination, for instance a human body, is foreseen with the cited attributes.

The system comprises a data acquisition unit, in particular a video camera apparatus, which preferably contains an image processing unit, and which captures at least a part of the body surface and generates image data of the body surface, so that in the meantime 3D position data, in particular the position and in some cases the orientation (in space) of an instrument inserted into the interior of an object under examination, in particular a body, in particular an endoscope, is captured by means of a position measuring system. By means of the 3D position data, a virtual model of the instrument inserted into the object under investigation is obtained, where in particular a number of 3D position data are captured by various portions of the object under examination, in particular the endoscope.

The system shows an evaluation unit, which connects the fed 3D position data with the fed image data in such a way that a virtual image of the instrument corresponding to the position and size of the image data is generated and it is preferably connected with the image data of the data acquisition unit or video camera apparatus, so that preferably a common augmented-reality image is provided.

Finally the image information obtained from the body surface image and the 3D position data are fed into an output unit and by means of said unit are displayed, for instance on a monitor. The produced image of the instrument or endoscope here is, corresponding to the position and size, preferably depicted in the body surface image, integrated in the manner of an augmented-reality image.

The displayed image shows, on the one hand, the surface of the object under examination, or body of the patient, and, on the other hand, a virtual image of the instrument or endoscope adapted to the size and position of the object under examination or patient's body. Preferably at least one body image is connected and displayed with the produced virtual endoscope image in real time with the inventive system.

Through this system it becomes possible, on the one hand, to obtain under time pressure a very intuitive and rapid capture of the orientation of the instrument even under difficult external circumstances such as in the course of a long and difficult operation or endoscopic examination. This makes possible a clearly less risky examination or operation on a patient, because treatment errors resulting from false orientation are largely excluded. The orientation is directly marked, in particular, by the linking of the virtual information on the position of the instrument with the well-known surface of the object under examination. Cumbersome and time-consuming preoperative CT examinations, therefore, are no longer obligatory.

According to the invention, it is also possible to avoid a typical problem arising from the fact that the preoperatively obtained planning data no longer correspond with the current situs. Thus, because of an intervening organ deformation, which has occurred after the obtaining of information for performing a computer-supported intervention, a completely new operating environment can prevail. In the area of soft-tissue operations, it is also entirely possible that, through intraoperative motion of the soft-tissue organs, it is no longer possible to implement the operation planning by a navigation system. These problems are overcome at least in part thanks to the inventive system, because the improved orientation is partially sufficient for successful conclusion of the operation. In addition, according to the invention this can occur in real time, something that is not possible with known systems with preoperatively produced data sets.

In another preferred embodiment of the system, the at least one virtual image of the instrument, in particular of an endoscope, is projected onto a projection surface in the examination room. In this case the projection surface can in particular be a wall of an operating room and therefore inside the sterile zone, while the projection unit is positioned outside the sterile zone, set off from it by a glass partition. This makes efficient sterilization of the system possible, without affecting the improved orientation capability.

As a preferred alternative, projection can occur onto the typically not planar surface of the object of examination, in particular a body. Thus the system comprises in addition a unit for capturing the topography at least of the area of the object of examination captured by the video camera device. The topographic data are fed to an evaluation unit along with the image data and 3D position data. In the context of the evaluation, image data are then generated that generate a real image of the instrument as a virtual image, in accordance with the size, position, and projection surface. This ensures that the projected image appears faithful to reality on the surface of the object under examination and thereby makes possible a very intuitive, accurate, and low-impact orientation of the user, in particular the operator. In particular, an anatomically and positionally correct display of the instrument is made possible onto the object under examination, which reliably allows an additional instrument to be inserted through the surface of the object under examination at a site defined by the projection.

A projection of the virtually produced image of the endoscope inserted in the body onto the surface of the object under examination, in particular onto the body surface of a patient, has the advantage that a physician, after applying the instrument and inserting it into a body orifice of the patient, can follow the current position of the instrument on the patient, in particular online, and the physician does not receive orientation or position information on a remote, additional screen during the operation, but rather by looking directly at the patient. The physician thus receives the impression of almost looking through the skin directly onto the inserted instrument. The physician is therefore also not unnecessarily distracted and therefore need not constantly keep turning his or her head back and forth from the patient to the display unit, a result that can also have a very positive effect on the orientation capability.

The capture of the topography is preferably determined by a strip-light projection process.

In another preferred embodiment of the inventive system, the position measuring system comprises at least one, and preferably more than three, sensor units for capturing the position and orientation of the instrument. These units are preferably configured as electromagnetic coils (sending or receiving coils) by means of which the position and orientation is ascertained in an external electromagnetic field. An example of such a sensor unit is realized in the "Aurora System" product of the NDI Company, announced in the flyer "NDI Aurora Electromagnetic Tracking System." Magnetic field sensors and inertia measuring systems have proven themselves as alternatives. If a series of electromagnetic coils, in particular, are distributed on the surface of the instrument, or integrated into it, and positioned along its length, then the course of the inserted instrument can be determined and displayed very reliably. It is precisely the electromagnetic coils that make possible in a simple manner a reliable and simultaneous determination of the particular position in space.

The sensor units of the inventive system are preferably distributed uniformly over a portion of the instrument, allowing a very good orientation concerning the total position of the instrument. Because each sensor unit is correlated firmly with the instrument, in particular with the shaft of the endoscope, conclusions can be drawn reliably from the 3D position of a sensor unit concerning the position of the instrument.

The sensor units are preferably connected with the instrument and positioned with varying density. In particular, the density in the distal end area of an endoscope is increased, resulting in even more reliable information on the position of the instrument in the working area. Precisely with flexible endoscopes, the advantage of a secure orientation in this area is very important, in particular for less experienced operators, since the instrument can vary extremely strongly in its orientation and consequently faulty orientations, and the resulting faulty treatments, can be avoided.

In the inventive system, the sensors can also be integrated in or on endoscopic instruments for endoscopic surgery. Here, such instruments can be, for instance, forceps or HF cutting devices. In another embodiment of the invention, a sensor unit can be integrated into an endoscopy capsule (endopill). This capsule is ingested by the patient and migrates through the patient's body. As a result the interior of the body is captured and documented. Thanks to the inventive system, the endoscopy capsule is displayed in its position in the body for better orientation of the operator in connection with the body. If it should become necessary to remove the endoscopy capsule surgically, then on the basis of the inventive display of the endoscopy capsule, the appropriate place for the intervention can be reliably determined. This advantage becomes particularly clear, in fact, through the inventive projection onto the body.

It has also proven useful to configure the system with an instrument that constitutes an implant, in particular a short-time implant. With the help of the inventive system, it is possible to reliably follow the insertion of the instrument into the body as well as its retention in the desired position and the removal or expulsion of the instrument in its implant configuration.

In addition, reliable sensor units can be positioned extracorporeally, for instance on the object under examination itself or in the examination area, preferably on a wall of this area, making possible a more exact referencing and thus position recognition of the inserted instrument. Especially preferred here have been extracorporeal sensors, which are positioned on the insertion area of the instrument in the object under examination and thus are captured in parallel by the data acquisition unit. This makes possible an especially secure referencing and thus a secure display of the correct position and orientation.

Especially advantageous is the use of reference markers, which not only make it possible to reference a component (for example, data acquisition unit, position measuring system, or unit for capturing topography) of the inventive system, but at the same time in several allow a referencing and advantageously a common unified referencing. This results in improvement in further processing of captured data that are based on a common reference (unified space coordinates).

Particularly in thin instruments such as catheters for operations, the inventive system shows strength, because these instruments in part can only be usefully operated with difficulty and, in the event of faulty operation, can cause relevant injuries to the patient. Such an orientation is particularly important here. Thus the sensor units are positioned in such a way that on pushing the instrument in the object under examination, all movements and any changes of direction, that is, all modifications of position and location, can be captured by the position measuring system and as a result the current position and orientation of the instrument can be ascertained.

In addition, the capture of image data by the data acquisition unit and the capture of 3D position data by the position measuring system are conducted preferably simultaneously and thus in synchronized manner. The ensuing evaluation of these data assures an effective display, which shows no undesired distortions because of time discontinuities of the data. The evaluation or display in this case can occur at a later time, in particular in discontinuous manner, and in particular not in real time.

On the other hand, if the acquisition and evaluation as well as the display are performed continuously and synchronously, as preferred, then an exact position determination and production of a virtual model of the endoscope are realized in connection with the image data, independently of the particular modification of the position of the object under examination and of the instrument in the object under examination, in particular by advancing the instrument. Preferably the time differences will be briefer than one second and preferably will lie in the range of milliseconds or less. The time control of the position measuring system and of the data acquisition unit and in some cases of the unit for capturing topography will be selected automatically, in particular depending on the examination situation, and not conducted by the operator.

Individual positions of the instrument and/or of the area for inserting the instrument into the object under examination (insertion channel), which are captured both by the measuring system and by the data acquisition system, are preferably used as extracorporeal reference point or reference points for the generation of image data that are correct in terms of position and size. Consequently, simple and rapid image data processing is ensured, because these reference points constitute fixed points in the adaptation of the image data and thereby the computational task can be considerably reduced. As a direct consequence, real-time systems can be achieved even without complex computational systems.

As a result of the invention, a system for orientation assistance of medical instruments is designed and produced, which permits an unpracticed/inexperienced user, preferably in real time, to receive a localization of the navigated instrument, which is close to reality and positionally correct, in connection with the image of the exterior of the patient, from an instrument inserted in the body, for instance an endoscope, by means of virtual imaging (augmented reality) and adapted to the current endoscope movement and endoscope positioning.

While advancing the instrument in the body, paying attention precisely either directly to the body of the patient as projected, or as merged in an extracorporeal body image of the patient captured on a monitor, the user thus receives visual information on the current placement/position of the instrument in the patient's body. The user thus receives a secure, rapid system, which causes significantly less radiation impact on the patient.

This type of system for orientation assistance and display of an instrument is relevant for new endoscopic techniques such as NOTES surgery or for the use of the endoscopic capsule or pill (endopill).

The inventive system for orientation assistance and display of an instrument in an object under examination, in particular an endoscope, as well as the manner of functioning of the individual units, is explained more closely hereafter with reference to individual embodiments in association with the illustrations. The invention is not restricted to these embodiments.

DETAILED DESCRIPTION OF THE INVENTION

Figure 1:
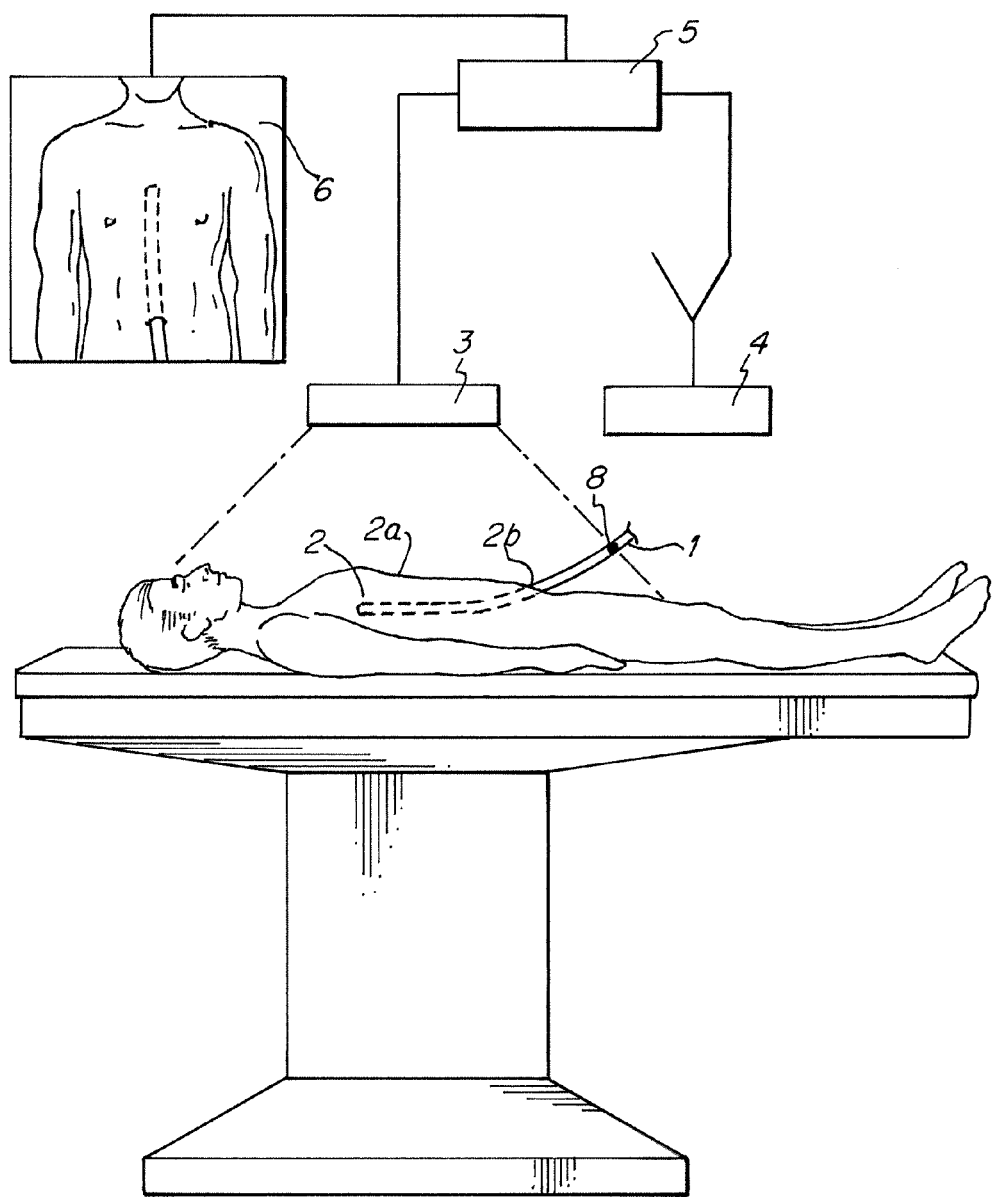
FIG. 1 is a schematic drawing of an inventive system.

FIG. 1 shows an execution of the inventive system on the basis of a schematic display of a surgical situation in a body 2 of a patient. According to this embodiment, an endoscope 1 is inserted into a human body 2 in the area of the patient's navel. The endoscope extends in the interior of the body 2 from the navel to the area of the heart, where the distal end of the endoscope 1 comes to rest. It is precisely during the endoscopy process, that is, at the start of the insertion of the endoscope into a body opening (entry channel) and the advancing of the endoscope to the site of the occurrence of the illness, that the patient or the surface of the patient's body is captured by means of an extracorporeal video camera device 3. In the process, the video camera device 3 is positioned directly above the patient and is equipped with a corresponding lens, which makes it possible for the entire duration of the intervention to reliably capture the part of the surface of the patient that is important for the operator. Such an arrangement and configuration of a video camera device has the advantage that it typically needs to be adjusted only once at the beginning of an intervention on the particular body and its individual surface, so that it is constantly possible to produce sharp, bright, and conclusive image data, which make possible an additional evaluation by the evaluation unit 5.

The inventive system further comprises a position measuring system 4 for capturing the position and orientation of the endoscope 1 equipped with sensor units 14. The position measuring system 4 shows sensor units 14, which are positioned integrated on or in the endoscope 1 and interact with extracorporeal units and from them derive information on the position of the sensor units 14 and consequently of the endoscope 1. The units of the position measuring system 4 use electromagnetic radiation to determine the position.

The frequency of this electromagnetic alternating field is allocated here in such a way that it can penetrate the human body largely without any disturbance. In addition, the sensor units 14 are of such dimensions that the electromagnetic field can be captured by these sensor units 14 with a good degree of effectiveness, so that massive disturbances of the signals are not a danger and thus a reliable determination of the position is assured. The signals of the position measuring system 4 are conducted to the evaluation device for further processing.

An evaluation device 5, not shown in further detail in FIG. 1, numerically links the signals of the position measuring system 4 with the image data 2.3 of the body surface 2a of the patient by the video camera device 3. In the process, information on the size and position or orientation of the body 2 of the patient is determined from the image data. The signals of the position measuring system 4 are used to generate 3D position data and to convert said data into a virtual image of the endoscope 1 and, in particular here, of the portion of the endoscope 1 inserted in the body 2 of the patient. This virtual image is thus adjusted in the orientation and size in such a way that it is combined with the image data to form a common image. An augmented-reality image emerges from a view of the body 2 of the patient, along with a virtual image, correct in terms of position, size and orientation, of the path of the endoscope 1 in the body 2. The virtual image of the endoscope 1 here is shown with dotted lines to distinguish it from the real image. The proximal part of the endoscope 1 captured by the video camera device 3 is not shown with dotted lines and includes a reference marker 8 for referencing. The two different images of the endoscope 1 collide with one another in the area of the body opening 2*b* through which the endoscope 1 is inserted.

By using reference points, which are captured jointly and simultaneously by the position measuring system 4 and the video camera device 3, it becomes possible, in a method that strongly reduces computer capacity and thus is rapid, to produce the aforementioned correct linking of the image data with the virtual image of the endoscope 1 in the evaluation unit 5. These reference points are quasi-fixed points in the linking of the data. The other data orient themselves around these data with a correct position, orientation, and size. It is especially advantageous to use two such reference points.

The result of the linkage is conducted to an output unit, such as a monitor 6, and there is put on display. The display is located at the operator's eye level.

The images displayed on the monitor 6 make it possible for the operator to become oriented very rapidly. This is particularly important in difficult, stressful operations. With less experienced operators as well, an improved operation result becomes possible thanks to the inventively improved orientation possibility. Through the inventive linkage of the virtual image of the instrument produced on the basis of the 3D position data with the image data of the body 2 of the patient captured by the extracorporeal video camera device 3, it becomes possible to achieve intuitively a rapid and reliable capture of the position of the instrument in the body and thereby to avoid erroneous treatments by an operator based on insufficient orientation in the body during the operation. Erroneous treatments can be reduced as a result.

Figure 2:
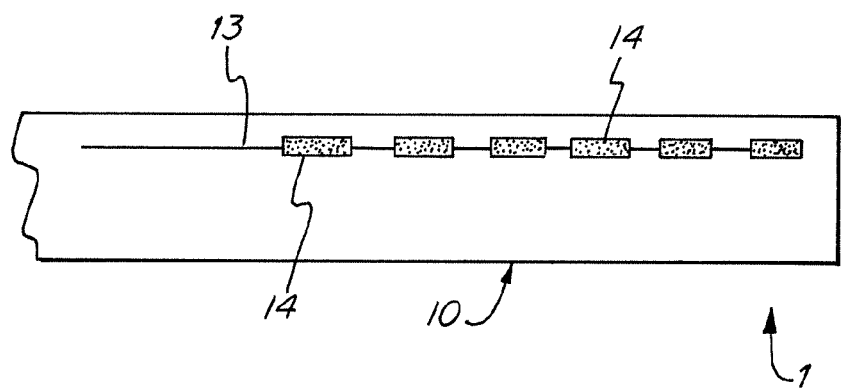
FIG. 2 shows an endoscope with an inventive arrangement of several sensor units.

FIG. 2 shows a medical instrument, an endoscope 1, with several cylinder-shaped sensor units 14 positioned in a row and integrated in the shaft 10 of the endoscope. Thanks to the integration, sterilization of the instrument becomes possible, something that is especially helpful to the customary handling by the operator and consequently reduces erroneous uses. These sensor units 14 are configured as small electromagnetic receptor coils. The sensor units 14 are connected with one another by a data line 13 and by this means can be supplied with energy. The sensor units 14 capture an external electromagnetic field, which is formed by extracorporeal emitter units that are produced as emitter coils. The positions of the sensor units 14 in space can be determined in awareness of the path of the electromagnetic field. This occurs during use of field strength information and/or running time information. The sensor units 14 here are distributed uniformly over a portion of the shaft 10 of the endoscope 1, so that its spatial path can be accurately determined. The portion is positioned in the area of the distal end of the shaft 10, allowing the especially relevant position of the working area of the endoscope 1 to be captured with particular reliability and consequently improving the operator's orientation as needed.

Instead of the cylindrical sensor units 14 shown here, it is also possible to select spherical or saddle-shaped sensor units 14 and to produce them from flexible materials that make it possible for a sensor unit 14 to adapt to the shape of the endoscope 1 and thereby to adapt to its form of tilting by the instrument 1 in the body 2. To determine the position of a sensor unit 14, a sensor unit does not necessarily have to be able only to receive signals, but can also be configured in such a way that it can itself emit signals for position determination and/or in addition receive them.

Figure 3:
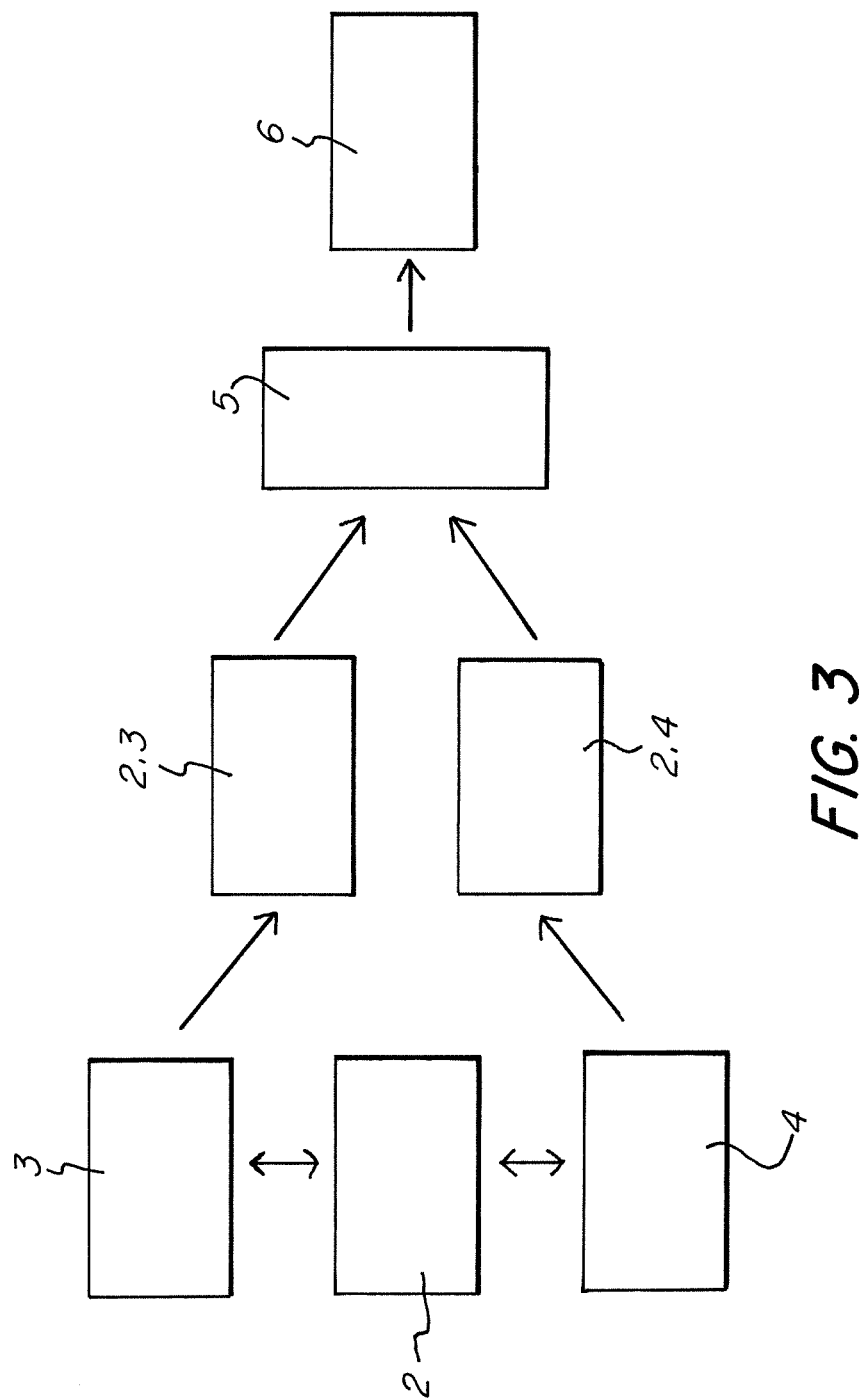
FIG. 3 is a block diagram of an inventive system arrangement.

FIG. 3 shows an example of the structure of the proposed system in the form of a block diagram. The system comprises in the illustrated example the following units or components: an external video camera device 3, a position measuring system 4, an evaluation unit 5, and an output unit 6.

The evaluation unit 5 is configured in such a way that image data 2.3 and 3D position data 2.4 can be conveyed to it by two interfaces. The image data 2.3 originate from a video camera device 3, which captures at least a part of the surface of the body and from it generates image data 2.3 of the captured surface. The 3D position data are provided by a position measuring system 4. The position measuring system 4 independently ascertains the position of the instrument 1 equipped with several sensor units 14 and generates corresponding 3D position data 2.4.

The evaluation unit 5, according to the invention, is configured in such a way that, from the majority of the 3D position data 2.4 of the sensor units 14 captured by the position measuring system 4, it can produce, at least partly, a virtual 3D model of the endoscope 1 from which a virtual 2D image of the intervening instrument is derived. In addition, the image data generated by the video camera device 3 and the individual 3D position data for producing a common augmented-reality image are linked with one another to generate an appropriate image display.

The evaluation unit 5 is connected with an output unit 6, for instance a monitor 6, on which the generated augmented-reality image can be displayed. With this system, video camera image data 2.3 and perspectival, visualized 3D position data 2.4 can be optimally linked in real time with one another and optically displayed on an output unit 6. The displayed system here consists of standardized components that lend themselves to being connected to form a common system simply and reliably. The operator thus is provided with a system for orientation support with which operations can potentially be performed more rapidly and, for the patient, more safely.

The invention claimed is:

1. A system for orientation assistance and display of an instrument in a patient under examination, the system comprising:

a data acquisition unit having a video camera device that is situated outside the patient under examination and that captures at least a part of the surface of the patient under examination and generates image data of the captured surface of the patient;

a position measuring system for ascertaining 3D position data of the instrument;

said position measuring system and said video camera device jointly and simultaneously capturing at least two reference points of the positions of the instrument and of the area for inserting the instrument into the patient under examination;

an evaluation unit, said evaluation unit using said reference points for linking the 3D position data of the instrument with the image data of the captured surface of the patient and generating virtual images of the instrument that corresponds in position and size to the image data of the captured surface of the patient; and an output unit for displaying the virtual images of the instrument generated by the evaluation unit;

wherein said position measuring system comprises at least one reference marker that is spatially separated from the instrument and positioned extracorporeally at a distance from the patient under examination, so that said at least one reference marker can be acquired for referencing;

wherein said data acquisition unit and said position measuring system capture their data synchronously and continuously, and wherein said at least two reference points are quasi-fixed points in linking the data synchronously and continuously captured by said data acquisition unit and said position measuring system;

wherein the position measuring system includes at least two sensor units and wherein the at least two sensor units are distributed evenly over a portion of the instrument or positioned in the instrument;

wherein the position measuring system includes at least two sensor units and wherein the at least two sensor units are positioned unevenly over a portion of the instrument, in particular in a higher density in the distal end region of the instrument.

2. The system of claim 1, wherein the output unit comprises a monitor by means of which images of the instrument generated by the evaluation unit and images of the video camera device are displayed together on a monitor corresponding to their position and size.

3. The system of claim 1, wherein the output unit comprises a projection unit by means of which images of the instrument corresponding to its position and size generated by the evaluation unit are projected on a projection surface.

4. The system of claim 1, wherein a unit is provided for capturing the surface path of the patient under examination and the evaluation unit is configured to adapt the image data to the surface path of the projection surface.

5. The system of claim 1, wherein the position measuring system comprises at least one sensor unit positioned in or on the instrument.

6. The system of claim 1, wherein the at least one reference marker is positioned on the surface of the patient under examination.

7. The system of claim 1, wherein the at least one reference marker is positioned on a wall of the examination area.

8. The system of claim 1, wherein the data acquisition unit and the position measuring system capture their data continuously and the evaluation and/or output of the data occurs precisely with respect to time in real time.

9. The system of claim 1, wherein the reference points include extracorporeal positions of the instrument that are jointly present in the image of the video camera device and in the 3D position data of the instrument, the reference points being used for generating the image of the instrument that corresponds to its position and size.

10. The system of claim 3, wherein the projection surface consists of the surface of the patient under examination.

11. The system of claim 3, wherein the projection surface is in the room where the patient is under examination and the projection unit is positioned outside the room where the patient is under examination.

12. The system of claim 3, wherein the projection surface is on a wall of the room where the patient is under examination.

13. The system of claim 5, wherein the at least one sensor unit is configured for producing and/or detecting an electromagnetic field and wherein the position of the at least one sensor unit is determined on the basis of the electromagnetic field produced or detected by the position measuring system.

14. The system of claim 7, wherein the instrument includes a catheter, a rigid or flexible endoscope, an instrument for endoscopic surgery, an endoscopic capsule, or an implant.

15. The system of claim 7, wherein the evaluation and/or output occurs not in real time with the data acquisition by said data acquisition unit and said position measuring system.

* * * * *